(12) United States Patent
Krawiec et al.

(10) Patent No.: US 11,712,346 B2
(45) Date of Patent: Aug. 1, 2023

(54) EXPANDABLE FUSION DEVICE WITH INTEGRATED DEPLOYABLE RETENTION SPIKES

(71) Applicant: GLOBUS MEDICAL, INC., Audubon, PA (US)

(72) Inventors: Catherine Krawiec, Conshohocken, PA (US); Damien Kahmer, Glenside, PA (US); George Yacoub, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/540,381

(22) Filed: Dec. 2, 2021

(65) Prior Publication Data

US 2023/0172722 A1 Jun. 8, 2023

(51) Int. Cl.
*A61F 2/44* (2006.01)
*A61F 2/30* (2006.01)

(52) U.S. Cl.
CPC .... *A61F 2/447* (2013.01); *A61F 2002/30477* (2013.01); *A61F 2002/443* (2013.01)

(58) Field of Classification Search
CPC .......... A61F 2/4455–2/447; A61F 2250/0048; A61F 2220/0008–2220/0016; A61F 2250/0004–2250/001
See application file for complete search history.

(56) References Cited

U.S. PATENT DOCUMENTS

| | | | | |
|---|---|---|---|---|
| 9,801,734 | B1 * | 10/2017 | Stein | A61F 2/447 |
| 11,173,044 | B1 * | 11/2021 | Jones | A61F 2/447 |
| 2017/0105844 | A1 * | 4/2017 | Kuyler | A61F 2/447 |
| 2017/0304080 | A1 * | 10/2017 | Lee | A61F 2/4611 |
| 2020/0008955 | A1 * | 1/2020 | Ashleigh | A61F 2/4455 |

\* cited by examiner

*Primary Examiner* — Julianna N Harvey
*Assistant Examiner* — Angel Roberto Mora-Velazquez

(57) ABSTRACT

Expandable fusion devices, systems, and methods. The expandable fusion device includes one or more integrated deployable retention spikes configured to resist expulsion of the device when installed in the intervertebral disc space. The implant may include upper and lower main endplates, an actuator assembly configured to cause an expansion in height of the upper and lower main endplates, and a sidecar assembly including a sidecar carrier, an upper carrier endplate pivotably coupled to an upper spike, and a lower carrier endplate pivotably coupled to a lower spike such that forward translation of the sidecar carrier pushes against the upper and lower carrier endplates, thereby deploying the upper and lower spikes.

17 Claims, 12 Drawing Sheets

EXPANDABLE FUSION DEVICE WITH INTEGRATED DEPLOYABLE RETENTION SPIKES

FIELD OF THE INVENTION

The present disclosure relates to surgical devices, and more particularly, to expandable fusion devices capable of being inserted between adjacent vertebrae to facilitate the fusion process and including integrated deployable retention spikes configured to prevent expulsion of the device.

BACKGROUND

Sagittal imbalance accompanied by one or more spinal pathologies is often treated through a combination of direct and indirect decompression. Indirect decompression may be achieved through the placement of an intervertebral cage. The combination of osteotomy of the posterior elements, placement of cage(s), and subsequent compression on a pedicle screw/rod construct can be used to restore segmental lordosis to the operative level, thus restoring sagittal balance to the region.

The midline-sacrificing intradiscal osteotomy technique involves osteotomy of the posterior elements and ligamentum flavum, and opening a wide access to underlying dural sac and the disc space. Osteotomes may be used to remove posterior osteophytes and the disc en-bloc. The anterior longitudinal ligament (ALL) is released via spreader or blunt dissection, and bi-lateral expandable cages are placed on a posterior lumbar interbody fusion (PLIF) trajectory. Rods are reduced into screws placed prior to the osteotomy, and the screws are compressed. As the screws are brought closer together, the vertebral bodies rock about the fulcrum created by the interbody spacers, and segmental lordosis is increased, yielding the desired correction.

Due to the corrective nature of the procedure, a hyperlordotic expandable cage with a high degree of adjustability is needed. A high lordotic profile cage may have an increased risk of anterior expulsion due to increased forces in the axial plane. Due to the resection of the anterior longitudinal ligament, the natural barrier that would prevent anterior expulsion out of the disc space is no longer there. As such, there exists a need for an expandable fusion device that includes one or more anti-expulsion features.

SUMMARY

To meet this and other needs, and in view of its purposes, the present application provides devices, systems, and methods for installing and expanding an interbody implant and deploying integrated retention spikes. The expandable implants may include one or more integrated retention spikes configured to deploy from the implant body to resist expulsion of the implant from the disc space. In addition, the expandable interbody implants may be configured to communicate implant information with a robotic and/or navigation system. For example, position and orientation of the implant may be communicated to the system. The implant may include internal electronic components configured to automatically adjust the implant height and/or lordosis and deploy the retention spikes. One or more of these features may help to minimize the size of the working corridor and minimize the number of instruments required to operate the implant.

According to one embodiment, an expandable implant includes upper and lower main endplates, an actuator assembly, and a sidecar assembly. The upper and lower main endplates are configured to engage adjacent vertebrae. The actuator assembly is configured to cause an expansion in height of the upper and lower main endplates. The sidecar assembly may include a sidecar carrier, an upper carrier endplate pivotably coupled to an upper spike, and a lower carrier endplate pivotably coupled to a lower spike. Forward translation of the sidecar carrier pushes against the upper and lower carrier endplates, thereby deploying the upper and lower spikes.

The expandable implant may include one or more of the following features. The upper carrier endplate may include a first tusk and the lower carrier endplate may include a second tusk. The first and second tusks may extend toward a front of the implant. The first and second tusks may be receivable in respective passageways in the upper and lower main endplates to thereby guide translation of the upper and lower carrier endplates. The first and second tusks may have a generally polygonal cross-section that corresponds to the shape and dimensions of the respective passageway. The first and second tusks may allow for translation of the upper and lower carrier endplates with respect to the main endplates along a main longitudinal axis of the implant but restricts all other translation and rotation. Each spike may extend from a proximal end coupled to the respective carrier endplate to a free end. The free end may be sharpened or pointed and configured to pierce bone. Each of the upper and lower main endplates may include a side extension portion defining a side channel. The side channels may house and guide the upper and lower spikes, respectively. Each spike may be connected to the respective carrier endplate with a pin, thereby providing a hinged coupling between the carrier endplate and the spike. When the carrier endplates move forward, the spikes may bottom out on the floor of the channels, rotating about an axis of the pins connecting the spike to the carrier endplate, and the spikes emerge from the top and bottom planes of the main endplates.

According to another embodiment, an expandable implant includes upper and lower endplates, an actuator assembly, a plurality of driving ramps, and a sidecar assembly. The upper and lower main endplates are configured to engage adjacent vertebrae. The actuator assembly includes a rotatable actuator having a shaft and a rotatable nut. The plurality of driving ramps includes a front ramp, a mid-ramp, and a rear ramp positioned along the shaft of the actuator. The upper and lower main endplates are engaged with the plurality of driving ramps. Rotation of the actuator and/or the nut causes movement of one or more of the driving ramps, thereby causing an expansion in height of the upper and lower main endplates. The sidecar assembly includes a sidecar carrier, an upper carrier endplate pivotably coupled to an upper spike, and a lower carrier endplate pivotably coupled to a lower spike. Forward translation of the sidecar carrier pushes against the upper and lower carrier endplates, thereby deploying the upper and lower spikes.

The expandable implant may include one or more of the following features. The rear ramp may include a bore for receiving the actuator assembly and a pair of arms positioned on opposite sides of the bore. The rear ramp may include a dovetail slot along an outside face of one arm. The sidecar carrier may include a corresponding dovetail that mates with the dovetail of the rear ramp, allowing the sidecar carrier to translate with respect to the rear ramp along a main longitudinal axis of the implant while restricting all other translation or rotation. The dovetail slot may decrease in height towards a back of the rear ramp. The rear ramp may include a retention tab configured to prevent retraction of the spikes by preventing movement of the sidecar carrier. The retention tab may be defined by a relief cut such that the retention tab protrudes outward from a side face of the rear ramp. When the sidecar carrier passes over the retention tab, the retention tab springs outwardly to prevent the sidecar carrier from travelling backwards. Each of the upper and lower main endplates may include a side extension portion defining a side channel. The side channels may house and guide the upper and lower spikes, respectively. When the sidecar carrier translates forward, the carrier endplates move forward, the spikes bottom out on a floor of the channels, rotating and driving the spikes outwardly from top and bottom planes of the main endplates.

According to another embodiment, an expandable implant includes upper and lower main endplates, an actuator assembly, and integrated retention spikes. The upper and lower main endplates are configured to engage adjacent vertebrae. The actuator assembly includes a rotatable actuator and a driving ramp positioned along the actuator configured to cause an expansion in height of the upper and lower main endplates. The integrated retention spikes are deployable from the upper and lower main endplates. The integrated retention spikes deploy when a sidecar carrier is translated forward, pushing against upper and lower carrier endplates that are pivotably coupled to the respective retention spikes. Anterior and posterior heights of the implant may be independently adjustable for continuous adjustment of height and lordotic profile. The retention spikes may maintain a constant penetration depth out of the upper and lower main endplates regardless of height or lordotic expansion.

According to another embodiment, an autonomous expandable implant includes a computing unit, upper and lower main endplates, a plurality of force sensors, an actuation assembly, a plurality of driving ramps, an electrical motor, and a power supply. The computing unit includes a processor with memory housed within the implant. The upper and lower main endplates are configured to engage adjacent vertebrae. The plurality of force sensors are housed in the upper and lower main endplates. The force sensors are configured for load distribution measurement. The actuation assembly includes a rotatable actuator having a shaft and a rotatable nut. The plurality of driving ramps are positioned along the shaft of the actuator and engaged with the upper and lower main endplates. The electrical motor is configured to rotate the actuator and/or the nut to move the driving ramps and expand the upper and lower main endplates. The power supply is configured for providing power to the electrical motor.

The autonomous expandable implant may include one or more of the following features. The implant may further include a sidecar assembly including a sidecar carrier, an upper carrier endplate pivotably coupled to an upper spike, and a lower carrier endplate pivotably coupled to a lower spike. Forward translation of the sidecar carrier pushes against the upper and lower carrier endplates, thereby deploying the upper and lower spikes. The implant may further include a linear motor configured to translate the sidecar carrier, to thereby deploy the upper and lower spikes. The computing unit may automatically inform the linear motor of a drive initiation and duration to deploy the upper and lower spikes. The plurality of driving ramps may include a front ramp, a mid-ramp, and a rear ramp positioned along the shaft of the actuator. The implant may further include a plurality of hall effect sensors located in the front and mid ramps configured to provide real time positional information of the implant to a robotic navigation system. The computing unit may automatically inform the electrical motors of a drive amount and duration to adjust the height and lordosis of the implant based on information obtained from the force sensors. The implant may further include a wireless communication unit configured for sending and receiving information to a robotic navigation system. The power supply may include a wireless charging receiver, and an inserter instrument may include a wireless charger configured to interface with the wireless charging receiver to power the implant.

According to another embodiment, an autonomous expandable implant includes a front nose and a rear end including a housing, a computing unit, upper and lower main endplates, a plurality of force sensors, an actuator assembly, a plurality of driving ramps, a pair of electrical motors, a sidecar assembly, a linear motor, and a power supply. The computing unit includes a processor with memory located within the housing. The upper and lower main endplates are configured to engage adjacent vertebrae. The plurality of force sensors are housed in the upper and lower main endplates. The force sensors are configured for load distribution measurement. The actuator assembly includes a rotatable actuator having a shaft and a rotatable nut. The plurality of driving ramps includes a front ramp, a mid-ramp, and a rear ramp positioned along the shaft of the actuator and engaged with the upper and lower main endplates. The pair of electrical motors are configured to independently rotate the actuator and the nut to move the driving ramps and expand the upper and lower main endplates. The sidecar assembly includes a sidecar carrier, an upper carrier endplate pivotably coupled to an upper spike, and a lower carrier endplate pivotably coupled to a lower spike. The linear motor is configured to translate the sidecar carrier, to thereby deploy the upper and lower spikes. The power supply is configured for providing power to the motors located within the implant.

The autonomous expandable implant may include one or more of the following features. The linear motor may be located behind the sidecar carrier in the housing. The implant may further include a plurality of hall effect sensors configured to provide real time positional information of the implant to a robotic navigation system. The hall effect sensors may be located in the front and mid ramps. The computing unit may be located in the rear ramp. The implant may further include a wireless communication unit located within the housing. The wireless communication unit may be configured for sending and receiving information to a robotic navigation system.

According to yet another embodiment, a system of autonomously controlling an expandable implant includes a robotic navigation system and an inserter. The expandable implant may include a computing unit, upper and lower main endplates, a plurality of force sensors, an actuator assembly, a plurality of driving ramps, an electrical motor, a sidecar assembly, a linear motor, and a power supply. The computing unit includes a processor with memory housed within the implant. The upper and lower main endplates are configured to engage adjacent vertebrae. The plurality of force sensors are housed in the upper and lower main endplates. The force sensors are configured for load distribution measurement. The actuator assembly includes a rotatable actuator having a shaft and a rotatable nut configured to cause an expansion in height of the upper and lower main endplates. The plurality of driving ramps are positioned along the shaft of the actuator and engaged with the upper and lower main endplates. The electrical motor is configured to rotate the actuator and/or the nut to move the driving ramps and expand the upper and lower main endplates. The sidecar assembly includes a sidecar carrier, an upper carrier endplate pivotably coupled to an upper spike, and a lower carrier endplate pivotably coupled to a lower spike. The linear motor is configured to move the sidecar carrier, to thereby deploy the upper and lower spikes. The power supply is configured for providing power to the motors. The robotic navigation system includes a moveable end effector and a display. The inserter is positionable in the end effector and configured to hold the expandable implant. The robotic navigation system may include a wireless receiver for receiving implant force and position information and a wireless transmitter for transmitting user input to the implant. The inserter may include an electromagnet and a wireless charger. The power supply may include a wireless charging receiver, and the wireless charger of the inserter may interface with the wireless charging receiver to power the implant. The electromagnet on the inserter may generate an electric field causing the hall effect sensors to detect the relative location of the driving ramps.

According to yet another embodiment, a method of adjusting the height and/or lordosis of an expandable implant and deploying integral retention spikes may include one or more of the following steps in any suitable order: (1) preparing an intervertebral disc space, for example, including a discectomy; (2) inserting an endoscopic tube into the disc space; (3) introducing the expandable implant through the tube and into the disc space in a collapsed configuration and seating it in an appropriate position in the intervertebral disc space; (4) deploying the retention spikes by translating the sidecar carrier toward the front end of the implant, thereby deploying the spikes; (5) expanding the implant in height and/or lordosis into the expanded position before or after deploying the spikes. In the case of an autonomous implant, the method may also include: (6) obtaining load distribution information from the force sensors in the endplates; (7) applying a magnetic field to the hall effect sensors in the mid and front ramps with an electromagnet, for example, on an inserter to determine the physical position of the endplates and implant; (8) powering a wireless charging receiver in the implant using a wireless charger, for example, on the inserter; (9) expanding the implant in height and/or adjusting lordosis using information from a computing unit in the implant and/or a robotic/navigation system to operate DC motors in the implant to drive internal actuators in the implant; (10) deploying the retention spikes by using information from a computing unit in the implant and/or a robotic/navigation system to operate a linear servo motor in the implant to move the sidecar carrier and deploy the spikes.

Also provided are kits including expandable fusion devices of varying types and sizes, rods, fasteners or anchors, k-wires, inserters and other tools and instruments, robotic and/or navigation systems, and other components.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION

Figure 1:
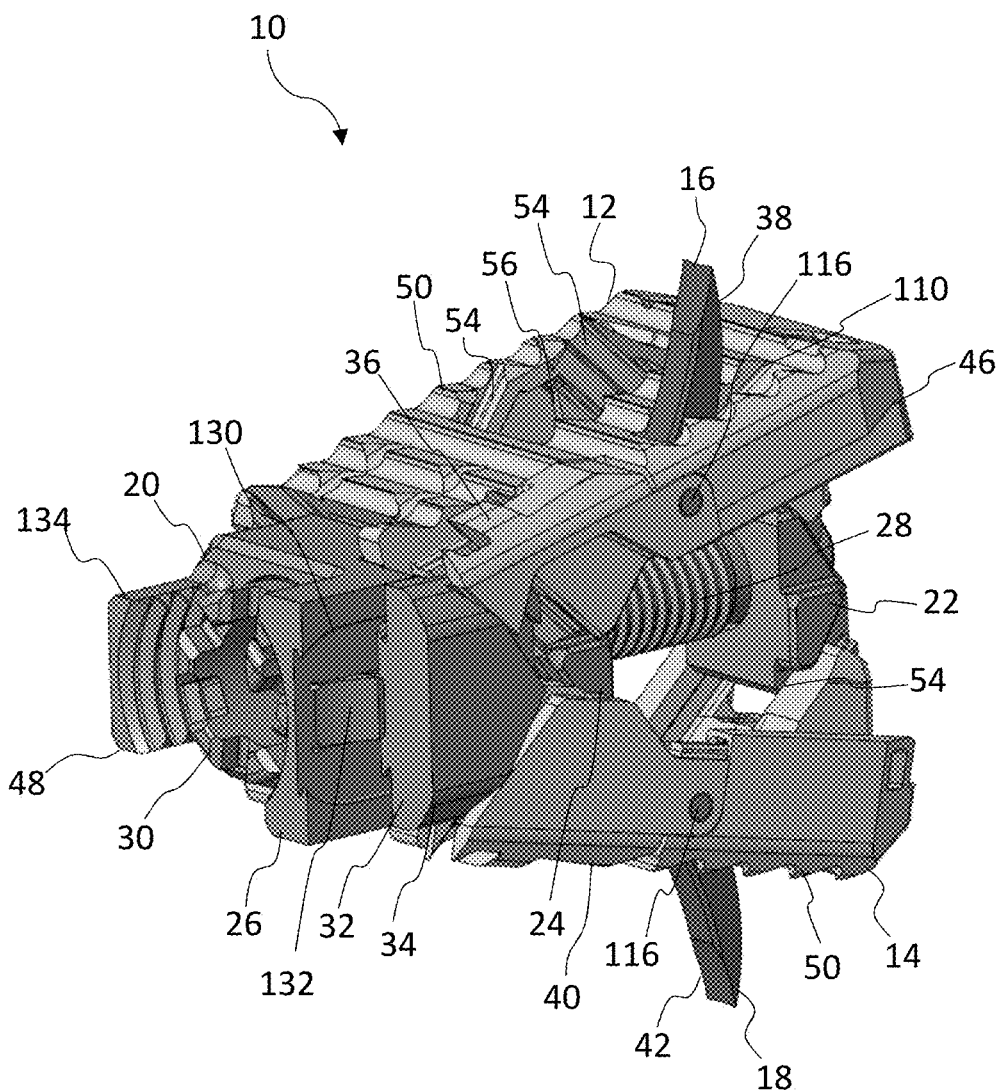
FIG. 1 is a perspective view of an expandable interbody implant in an expanded, lordotic position with integrated deployable retention spikes fully deployed according to one embodiment.

Embodiments of the disclosure are generally directed to expandable interbody devices, systems, and methods. Specifically, embodiments are directed to expandable interbody implants having integrated retention spikes configured to deploy from the implant body to resist expulsion of the implant from the disc space. The expandable interbody implants may be configured to communicate implant information with a robotic and/or navigation system. For example, position and orientation of the implant may be communicated as the implant expands. In addition, the implant may be configured to automatically adjust its height and lordosis and deploy the retention spikes with internal electronic components. These features may minimize the size of the working corridor and minimize the number of instruments required to operate the implant. The terms implant, interbody, interbody implant, fusion device, spacer, and expandable device may be used interchangeably herein.

Referring now to FIGS. 1-14, an expandable interbody implant 10 is shown according to one embodiment. The expandable interbody implant 10 includes an expandable interbody spacer with integrated deployable retention spikes 16, 18. The expandable implant 10 may include a first main or upper endplate 12, a second main or lower endplate 14, a first or upper deployable spike 16, and a second or lower deployable spike 18. The upper and lower spikes 16, 18 are configured to be deployed by a sidecar assembly 32, which may include a sidecar carrier 34 configured to move an upper carrier endplate 36 coupled to upper anchor or spike 38 and a lower carrier endplate 40 coupled to lower anchor or spike 42. The main upper and lower endplates 12, 14 and upper and lower carrier endplates 36, 40 are configured to be expanded by an actuator assembly 20, which may include a front ramp 22, a middle ramp 24, and a rear ramp 26 moveable via an actuator or central drive screw 28 and an outer drive screw or nut 30.

The anterior and posterior heights of the implant 10 may be independently adjustable for continuous adjustment of height and lordotic profile. The retention spikes 16, 18 maintain constant penetration depth out of the implant endplates 12, 14 regardless of height or lordotic expansion. The retention spikes 16, 18 may be deployed prior to implant expansion by pushing sidecar carrier 34 forward, driving the spikes 16, 18 through channel 110 in the main implant endplates 12, 14. When the sidecar carrier 34 is advanced to its final forward position, a retention tab 132 un-depresses, locking the carrier 34 in the forward position. The carrier endplates 36, 40 engage with the main endplates 12, 14 and follow their movement through height and lordotic expansion.

The implant 10 has a nose or front end 46 configured to be inserted first into a disc space between adjacent vertebral bodies and a back or rear end 48 configured to be coupled to an instrument for insertion and/or actuation of the actuator assembly 20. In one embodiment, the expandable implant 10 is configured to be placed down an endoscopic tube during a minimally invasive surgical (MIS) procedure and into the disc space. The expandable implant 10 may be inserted in a collapsed or contracted position and subsequently expanded in height and/or lordosis. The anchors or spikes 38, 42 may be deployed into the adjacent vertebral bodies to provide stability and prevent expulsion from the disc space.

The expandable fusion device 10 and components thereof may be manufactured from a number of biocompatible materials including, but not limited to: titanium, stainless steel, titanium alloys, non-titanium metallic alloys, polymeric materials, plastics, plastic composites, PEEK, ceramic, and elastic materials.

Figure 11:
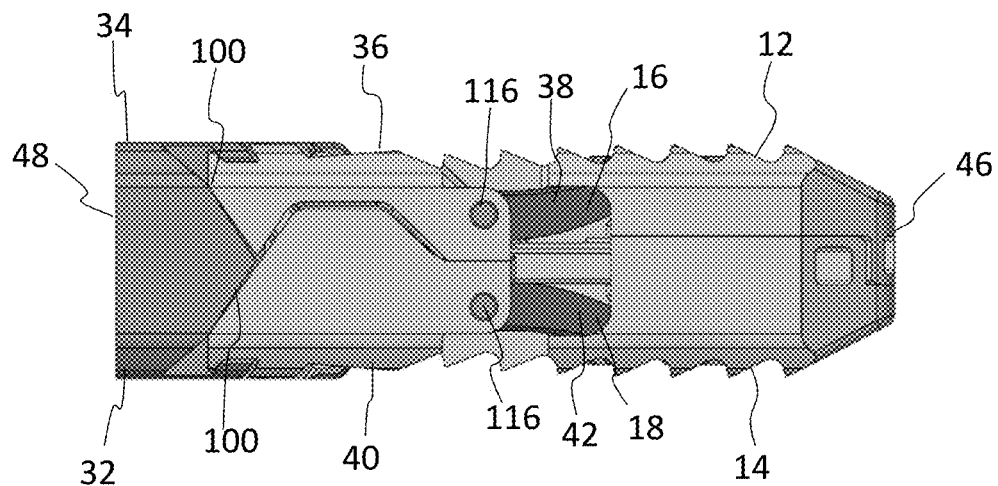
FIG. 11 shows a side view of implant in the collapsed position with the retention spikes contracted inside the body of the implant.

The main upper and lower endplates 12, 14 and upper and lower carrier endplates 36, 40 are configured to engage with adjacent vertebrae. As best seen in FIG. 1, the upper endplate 12 and upper carrier endplate 36 are nested together to form an entire upper endplate of the device 10. Similarly, the lower endplate 14 and lower carrier endplate 40 are nested together to form an entire lower endplate of the device 10. As best seen in FIG. 11, the upper endplates 12, 36 and lower endplates 14, 40 are also configured to nest or intermesh together in the collapsed position such that the overall height of the implant is minimized in the collapsed position. The upper endplate 12 and upper carrier endplate 36 will be described in further detail although it will be understood that the description applies equally to the lower endplate 12 and lower carrier endplate 40.

The upper endplate 12 may include an upper or outer surface 50 configured to contact bone and a lower or inner surface 52 opposite to the outer surface 50. The outer surface 50 may include a plurality of teeth, ridges, gripping or purchasing projections, keels or other texturing or friction increasing elements to aid in gripping the adjacent vertebral bodies. The inner surface 52 may define one or more ramps 54 configured to slidable interface with one or more corresponding ramps 84, 86, 88 on the front ramp 22, mid ramp 24, and/or rear ramp 26, thereby providing for expansion in height of the endplates 12, 14. The endplate 12 may define a through opening 56 extending between the outer and inner surfaces 50, 52 or a portion thereof. The through opening 56 may be configured to receive bone graft or similar bone growth inducing material to further promote and facilitate the intervertebral fusion.

Figure 2:
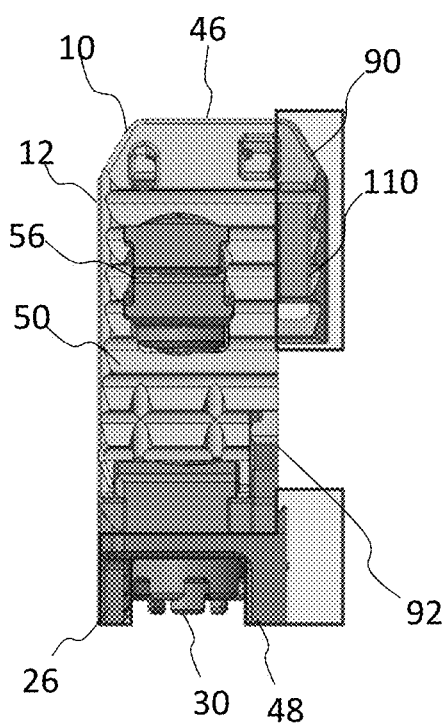
FIG. 2 is a top-down view of the expandable interbody implant with the sidecar carrier assembly omitted for clarity.
Figure 3:
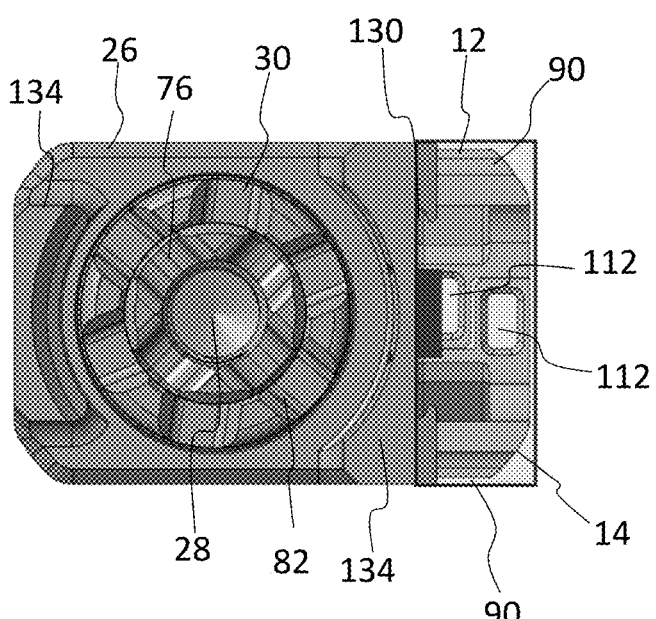
FIG. 3 is a rear view of the expandable interbody implant with the sidecar carrier assembly omitted for clarity.

As best seen in FIG. 2, which omits the sidecar carrier assembly 32 for clarity, the endplate 12 defines an extension portion 90 near the front end 46 of the endplate 12. The extension portion 90 is a side projection, which protrudes outwardly on one side of the endplate 12, thereby widening the footprint of the device 10. The extension portion 90 defines a recessed area 92 on the side of the device 10 near the rear end 48. The recessed area 92 is sized and dimensioned to receive the body of the upper carrier endplate 36. Although a right-side extension portion 90 and recess 92 is shown for accommodating the upper carrier endplate 36, it will be appreciated that the extension 90 and recess 92 could be provided on the opposite side.

Figure 7:
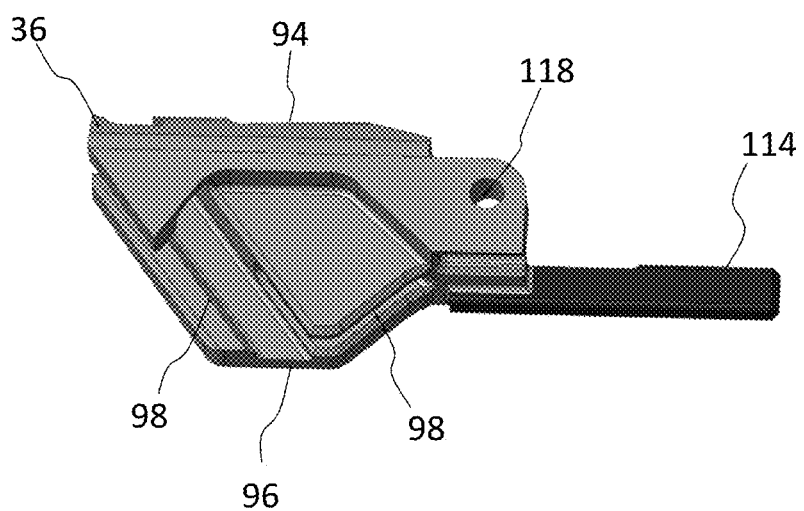
FIG. 7 is a perspective view of a sidecar carrier endplate and tusk for deploying the retention spike according to one embodiment.

As best seen in FIG. 7, the upper carrier endplate 36 includes a body with an upper or outer surface 94 configured to contact bone and a lower or inner surface 96 opposite to the outer surface 94. The outer surface 94 may include one or more teeth, ridges, gripping or purchasing projections, keels or other texturing or friction increasing elements to aid in gripping the adjacent vertebral bodies. The inner surface 96 may define one or more ramps 98 configured to slidable interface with one or more corresponding ramps 86, 100 on the middle ramp 24 and/or the sidecar carrier 34, thereby providing for expansion in height of the carrier endplates 36, 40 in tandem with the upper and lower main endplate 12, 14.

Figure 4:
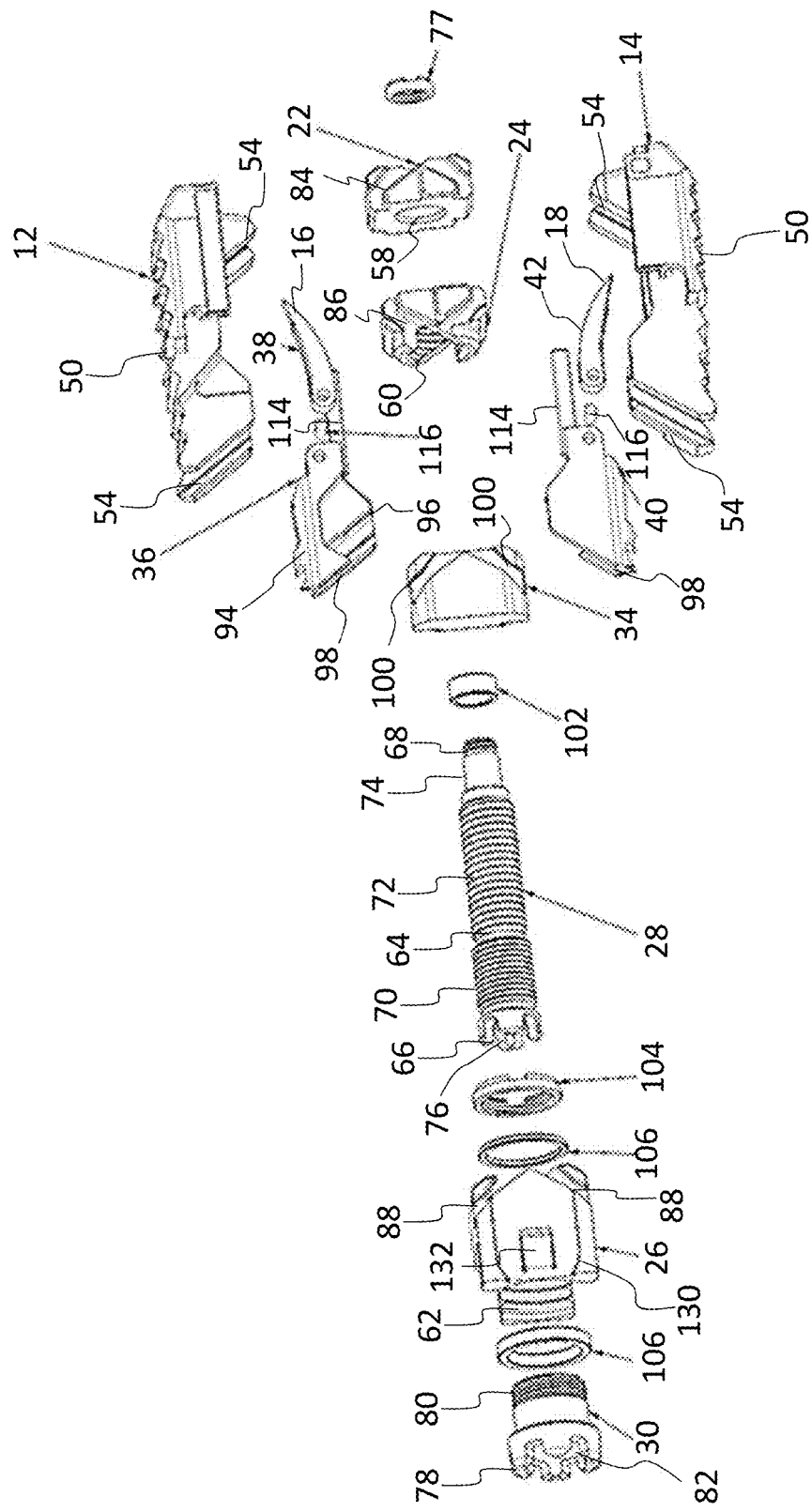
FIG. 4 is an exploded view of the expandable interbody implant.

With further emphasis on FIG. 4, the upper and lower endplates 12, 14 and upper and lower carrier endplates 36, 40 are configured to be expanded by an actuator assembly 20, which is configured to move a plurality of driving ramps 22, 24, 26 to expand the endplates 12, 14 and upper and lower carrier endplates 36, 40 in height. The actuator assembly 20 may include a front ramp 22, a middle ramp 24, and a rear ramp 26 moveable via an actuator or central drive screw 28 and an outer drive screw or nut 30. The front ramp 22 may include a central longitudinal bore 58, the mid-ramp 24 may include a central longitudinal bore 60, and the rear ramp 26 may include a central longitudinal bore 62. The plurality of driving ramps 22, 24, 26 may be positioned along the length of the actuator 28 and are configured to engage and drive the upper and lower endplates 12, 14, respectively. When one or more of the driving ramps 22, 24, 26 are moved, they slide against the upper and lower endplates 12, 14 and/or upper and lower carrier endplates 36, 40, thereby providing for expansion in height. The expansion may include the ability to individually adjust the anterior and/or posterior heights of the endplates 12, 14.

The implant 10 includes an expansion assembly 20. The expansion platform includes two main endplates 12, 14, both interlocking symmetrically with rear, middle, and front ramps 22, 24, 26, which are aligned coaxially along the central drive screw 28 such that the front ramp 22 is fixed translationally along the axis of the central drive screw 28 via the front locking nut 77 and front bushing 102. The rear and middle ramps 24, 26 are free to translate along the axis of the central drive screw 28, the middle ramp 24 being driven by rotation of the central drive screw 28. The central drive screw 28 is located concentrically within the outer drive screw 30, is free to translate along the axis of the outer drive screw 30, and may be driven by the outer drive screw 30. The outer drive screw 30 is seated within the axial hole 62 in the rear ramp 26, and is translationally fixed with respect to the rear ramp 26 via the rear locking nut 104. Bushings 106 may act as bearing surfaces for the rotational motion. The relative motion of the front and middle ramps 22, 24 may cause the main endplates 12, 14 to expand and contract such that the anterior and posterior heights change at the same rate. The relative motion of the front and rear ramps 22, 26 may cause the main endplates 12, 14 to expand such that the posterior height decreases and the anterior height increases.

The actuation assembly 20 is configured to independently expand the respective heights of the endplates 12, 14 and associated upper and lower carrier endplates 36, 40. The actuation assembly 20 includes rotatable actuator or central drive screw 28 and rotatable nut or outer drive screw 30 configured to move the plurality of internal ramps 22, 24, 26. The three driving ramps: front ramp 22, mid-ramp 24, and rear ramp 26 interface with the actuator 28. The actuator 28 may include a shaft 64 extending from a proximal end 66 to a distal end 68. The shaft 64 may include a first threaded portion 70, a second threaded portion 72, and a non-threaded portion 74. The second threaded portion 72 may be positioned between the first threaded portion 70 and the non-threaded portion 74. The threaded portions 70, 72 may have the same or different attributes including outer diameters, handedness, thread form, thread angle, lead, pitch, etc.

The front driving ramp 22 includes through bore 58, and the front driving ramp 22 is positioned on the non-threaded portion 74 of the actuator 28. The mid-ramp 24 includes a threaded bore 60, and the mid-ramp 24 is positioned on the second threaded portion 72 of the actuator 28. The mid-ramp 24 is threadedly moveable along the length of the second threaded portion 72 of the actuator 28. The rear ramp 26 is engaged with the nut 30, which is positioned along the first threaded portion 70 of the actuator 28 and is moveable along the length of the first threaded portion 70. The middle and rear driving ramps 24, 26 are each moveable along their respective threaded portions 72, 70 to move the upper and lower endplates 12, 14 and/or upper and lower carrier endplates 36, 40, and thereby expand the implant 10 in height. The threaded portions 70, 72 and non-threaded portion 74 may have the same or different outer diameters. The threaded portions 70, 72 may have the same or different threaded attributes or handedness. The proximal end 66 of the actuator shaft 64 may include a first instrument retention recess 76, for example, with a slotted head. The instrument recess 76 may include one or more alternating fingers and slots, ribs, knurled grips, or other suitable engagement surfaces, which are configured to interface with a driver instrument to thereby rotate the actuator shaft 28. The distal end 68 of the actuator shaft 28 may be externally threaded to receive internally threaded locking nut 77 configured to secure the front ramp 22 to the actuator 28.

The actuation assembly 20 may include rotatable nut or outer drive screw 30. The rotatable nut 30 may be configured to move the rear ramp 26 independent of the mid-ramp 24 and front ramp 22. The nut 30 may extend from a proximal end 78 to a distal end 80. The proximal end 78 may include a second instrument retention feature, such as a slotted head 82. The slotted head 82 may include fingers and slots or other suitable engagement surfaces configured to interface with a driver instrument to thereby rotate the nut 30. The distal end 80 may be externally threaded to mate with internally threaded rear locking nut 104. When only the nut 30 is rotated, the rear ramp 26 may be translated forward such that the posterior height increases. When the nut 30 remains stationary and only the actuator 28 is rotated, the rear ramp 26 and the mid-ramp 24 may both move backward such that the anterior height increases. When both the actuator 28 and the nut 30 are rotated at the same time mid-ramp 24 may move backward, thereby moving the endplates 12, 14 in parallel. It will be appreciated that the movement of the driving ramps 22, 24, 26 and resulting expansion may be operated by the actuator 28 and/or nut 30 with any suitable configurations and mechanisms.

The driving ramps 22, 24, 26 engage with upper and lower endplates 12, 14 and associated upper and lower carrier endplates 36, 40 to thereby move the upper and lower endplates 12, 14 and upper and lower carrier endplates 36, 40 outwardly in height and/or lordosis.

Figure 5:
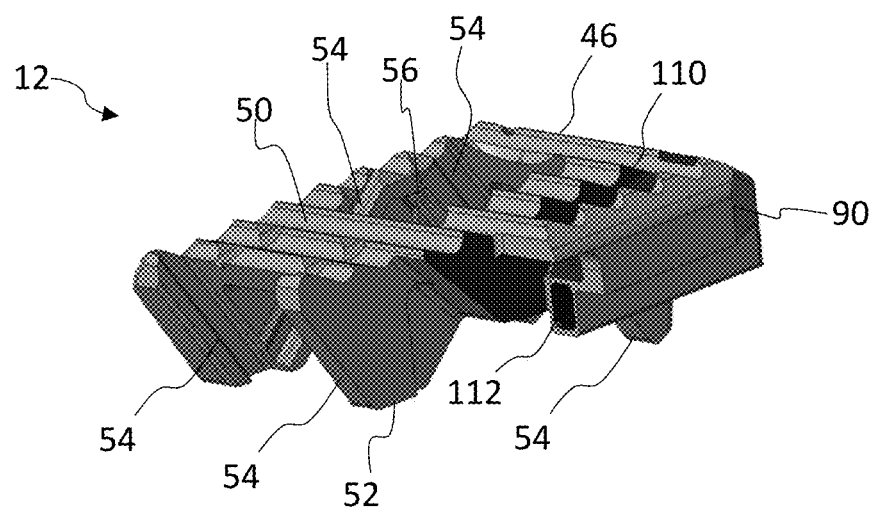
FIG. 5 is a perspective view of an upper main endplate according to one embodiment.

As best seen in FIGS. 5 and 7, the upper endplate 12 includes inner surface 52 configured to mate with the driving ramps 22, 26 and the upper carrier endplate 36 includes inner surface 96 configured to mate with driving ramp 24. The inner surfaces 52, 96 may include one or more ramped surfaces 54, 98. For example, the upper endplate 12 may include at least one first ramped surface 54 near the front 46 of the device 10, at least one second ramped surface 54 near the rear 48 of the device 10, and at least one third ramped surface 54 between the first and second ramped surfaces 54. For example, the endplate 12, 14 may include a pair of first ramped surfaces 54, a pair of second ramped surfaces 54, and a pair of third ramped surfaces 54 oriented to engage the respective ramps 22, 24, 26.

The upper carrier endplate 36 may include at least one first ramped surface 98 facing the front 46 of the device 10 and at least one second ramped surface 98 facing the rear 48 of the device 10. The sidecar carrier 34 includes at least one ramped surface 100. For example, an outside face of the sidecar carrier 34 may define a first upper ramped surface 100 and a second lower ramped surface facing toward the front 46 of the implant 10. The sidecar carrier 34 may include a ramp geometry that mimics that of the rear ramp 26. In one embodiment, the first ramped surfaces 98 of the upper carrier endplate 36 facing the front 46 of the device 10 may be configured to slidably interface with the ramps 86 of the mid driving ramp 24. The second ramped surfaces 98 facing the rear 48 of the device 10 may be configured to slidably interface with the ramps 100 of the sidecar carrier 34. In this manner, the upper endplate 12 and the upper carrier endplate 36 may act as one unit during expansion, thereby engaging with the adjacent vertebral body.

The ramped surfaces 54, 98 may be angled continuous surfaces with a given angle of slope. It is contemplated that the slope of the ramped surfaces 54, 98 may be equal or can differ from each other. The ramped surfaces 54, 98 may be generally straight ramped surfaces or may be curved ramped surfaces. The ramped surfaces 54, 98 may include male slide ramps or protruding ramps. The ramped surfaces 54, 98 may be spaced apart at an equal distance such that the ramped surfaces are substantially parallel to one another. Although a specific arrangement of ramped surfaces is shown, it is envisioned that the number, location, and configuration of ramped surfaces may be modified or selected by one skilled in the art.

The driving ramps 22, 24, 26 may include one or more ramped surfaces 84, 86, 88. The ramped surfaces 84, 86, 88 of the driving ramps 22, 24, 26 may be configured and dimensioned to engage the corresponding ramped surfaces 54, 98 of the upper and lower endplates 12, 14 and upper and lower carrier endplates 36, 40, respectively. For example, the front ramp 22 may include one or more ramped surfaces 84, mid-ramp 24 may include one or more ramped surfaces 86, and rear ramp 26 may include one or more ramped surfaces 88. For example, the front ramp 22 may include a first pair of upper ramped surfaces 84 and a second pair of lower ramped surfaces 84. The mid-ramp 24 may include a first pair of upper ramped surfaces 86 and a second pair of lower ramped surfaces 86. The rear ramp 26 may include a first pair of upper ramped surfaces 88 and a second pair of lower ramped surfaces 88. The ramped surfaces 84, 86, 88 may be angled continuous surfaces with a given angle of slope. It is contemplated that the slope of the ramped surfaces 84, 86, 88 may be equal or can differ from each other.

The ramped surfaces 84, 86, 88 may be generally straight ramped surfaces or may be curved ramped surfaces. The ramped surfaces 84, 86, 88 may include female slide ramps or recessed ramps configured to receive the male ramped surfaces 54, 98 of the upper and lower endplates 12, 14 and upper and lower carrier endplates 36, 40, respectively. A dovetail type connection may be formed between the ramped surfaces for stability and reliability, although other mating and sliding engagements can be used. It will be appreciated that the male and female ramps may be reversed or may be otherwise configured to provide for slidable mating between the ramps.

The front ramped surface(s) 54 of the endplate 12, 14 may be configured to slidably interface with the ramped surface(s) 84 of the front driving ramp 22. The rear ramped surface(s) 54 of the endplate 12, 14 may be configured to slidably interface with the ramped surface(s) 88 of the rear ramp 26. The middle ramped surface(s) 54 of the endplate 12, 14 and/or ramped surface(s) 98 of the carrier endplate 36, 40 may be configured to slidably interface with the ramped surface(s) 86 of the mid-ramp 24. As one or more of the driving ramps 22, 24, 26 moves, the ramped surface or surfaces 84, 86, 88 pushes against the corresponding ramped surface or surfaces 54, 98 of the upper and lower endplates 12, 14 and upper and lower carrier endplates 36, 40. In this manner, the individual driving ramps 22, 24, 26 control the rate of expansion of the upper and lower endplates 12, 14 and upper and lower carrier endplates 36, 40. The upper and lower endplate 12, 14 and upper and lower carrier endplates 36, 40 are pushed outwardly into one of the expanded configurations.

With further emphasis on FIGS. 11-14, the implant 10 has a spike-deployment assembly 32 configured to deploy upper and lower spike assemblies 16, 18. The upper spike assembly 16 includes upper spike 38 hingedly connected to upper carrier endplate 36 and lower spike assembly 18 include lower spike 42 hingedly connected to lower carrier endplate 40. The spike-deployment assembly 32 may include sidecar carrier 34 interlocked with the upper and lower carrier endplates 36, 40. The presence of retention spikes 38, 42 prevents expulsion to a higher degree than a spacer with no expulsion-resistant features. The integration of retention spikes 38, 42 inside the implant 10 reduces the number of steps to deploy the spikes 38, 42 and allows for deployment with the same inserter used to place the spacer 10.

Figure 6:
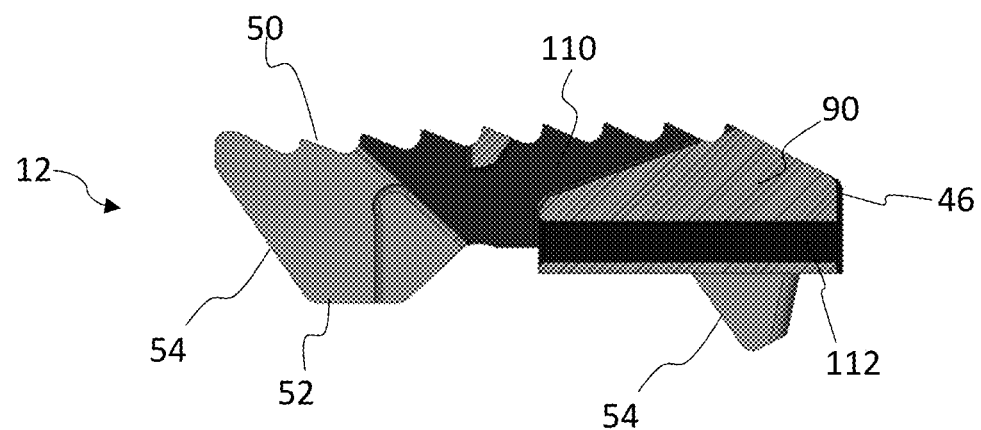
FIG. 6 is a cross-sectional view of the upper endplate of FIG. 5.

With further emphasis on FIGS. 5 and 6, the spikes 38, 42 are configured to be deployed through the main endplates 12, 14. The main endplates 12, 14 include an elongated side channel 110 that houses and guides the spikes 38, 42. Each endplate 12, 14 defines channel 110 through the extension portion 90 of the endplate 12, 14 along the main longitudinal axis of the implant 10. The channel 110 is sized and dimensioned to house, guide, and deploy the respective spike 38, 42. The extension portion 90 further defines passage 112 for receiving tusk 114 of the carrier endplate 36, 40.

With further emphasis on FIG. 7, each carrier endplate 36, 40 includes an elongate tusk 114 extending toward the front 46 of the implant 10. The tusk 114 may have a polygonal cross-section, for example, a generally square or rectangular shape which corresponds to the shape and dimensions of the passage 112. The tusk 114 may be integral with the carrier endplate 36, 40 or may be coupled thereto in a suitable manner. The top and bottom carrier endplates 34, 40 are constrained to the top and bottom main endplates 12, 14, respectively, via tusks 114 that extend from the leading edge of the carrier endplates 36, 40 and inserts into respective passageways 112 in the main endplates 12, 14. The tusk 114 allows for translation of the carrier endplates 36, 40 with respect to the main endplates 12, 14 along the main longitudinal axis of the device 10, but restricts all other translation and rotation.

Figure 9:
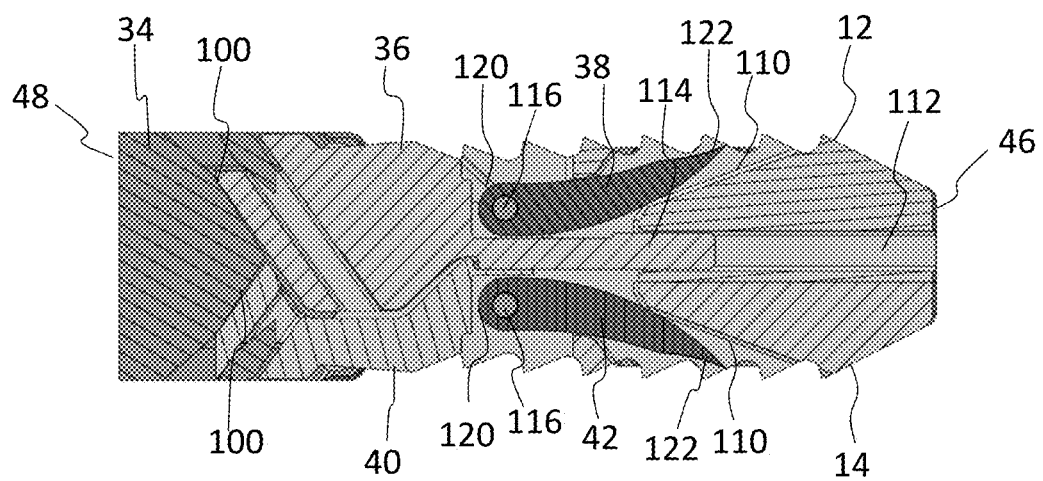
FIG. 9 is a cross-sectional view of the implant in a collapsed position with the integrated retention spikes contracted into the body of the implant.
Figure 10:
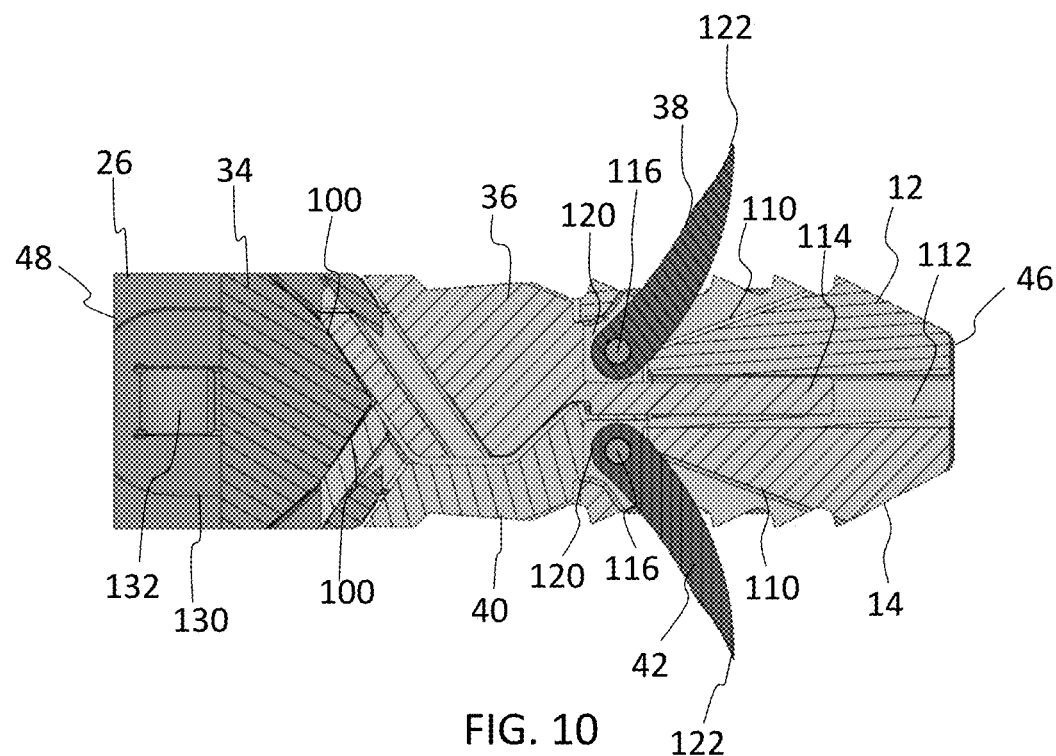
FIG. 10 is a cross-sectional view of the implant in the collapsed position with the retention spikes deployed.

As shown in FIGS. 9 and 10, each spike 38, 42 may be connected to the respective carrier endplate 36, 40 with a pin 116. The pin 116 may be receivable through opening 118 in the carrier endplate 36, 40 to provide a pivotable coupling between the endplate 36, 40 and the spike 38, 42. The anchor or spike 38, 42 may extend from a proximal end 120 coupled to endplate 36, 40 to a distal or free end 122. The free end 122 of the spike 38, 42 may have a pointed or sharp end 122 configured to pierce bone. The spike 38, 42 may be curved or contoured along its body such that the spikes 38, 42 travel further outwardly as they are deployed. Although a curved spike is exemplified, the spike 38, 42 may include any suitable anchor, shim, or fastener configured to resist expulsion of the device 10.

As the carrier endplates 36, 40 advance forward toward the main endplates 12, 14, the tusks 114 travel through passages 112, and the spikes 38, 42 travel through the cut-out channels 110 in the main endplates 12, 14. As the carrier endplates 36, 40 move forward, the spikes 38, 42 bottom out on the respective floors of the channels 110, rotating the spikes 38, 42 about the axis of the respective pins 116 connecting the spike 38, 42 to the carrier endplate 36, 40. As best seen in FIG. 10, the spikes 38, 42 emerge from the top and bottom planes of the main endplates 12, 14, thereby deploying the spikes 38, 42 outwardly into the adjacent vertebral bodies.

Although pins 116 are exemplified, it will be appreciated that attachment and capture of the spikes 38, 42 may be achieved in a number of ways. In the embodiment provided herein the spikes 38, 42 are captured by walls in the carrier endplates 36, 40 and pinned. This arrangement may also be achieved by incorporating a pin-like post off the side of the spike itself, which may reduce the need for an additional component. The attachment may also be accomplished by a threaded ball-and-socket interface that allows a threaded ball on the end of the spike to be threaded into an internally threaded spherical socket, for example.

Figure 8:
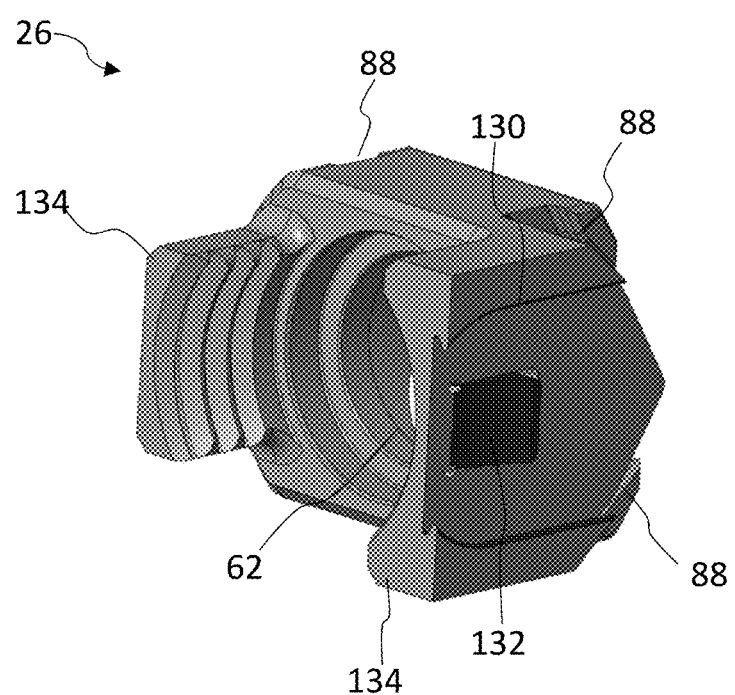
FIG. 8 is a perspective view of the rear ramp with dovetail and retention tab according to one embodiment.

With further emphasis on FIG. 8, the rear ramp 26 may include a dovetail 130 and retention tab 132 to direct and lock motion of the sidecar carrier 34. The rear ramp 26 may include a pair of arms 134 about bore 62. An inner surface of each arm 134 may define a threaded portion, for example, configured to engage with an instrument. One arm 134 of the rear ramp 26 may define the dovetail slot 130 along an outer side face of the ramp 26. The carrier 34 has a corresponding dovetail that mates with the dovetail slot 130 of the rear ramp 26, allowing the carrier 34 to translate with respect to the rear ramp 26 along the main longitudinal axis of the device 10 while restricting all other translation or rotation. The dovetail 130 may follow a path whose height decreases towards the rear of the rear ramp 26, such that the carrier 34 is captured and unable to back all the way out of the ramp 26.

Figure 12:
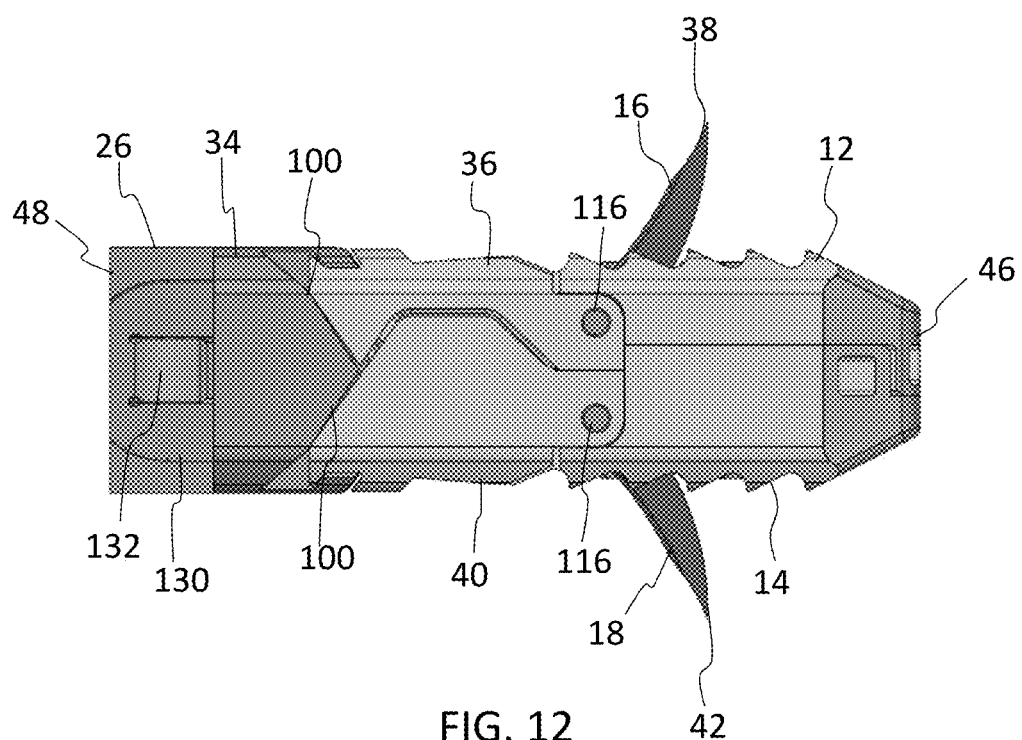
FIG. 12 shows a side view of the implant in the collapsed position with the retention spikes deployed.

The retention tab 132 may act as an automatic lock to prevent retraction of the spikes 38, 42 after deployment. The retention tab 132 may be formed of relief cut that defines a polygonal tab, such as square or rectangular tab. The tab 132 may be configured to protrude outward, for example, toward the front end 46 of the implant 10. In this manner, when the sidecar carrier 34 passes over the tab 132, the tab 132 springs outwardly to prevent the sidecar carrier 34 from travelling back toward the rear end 48 of the implant 10. When the spike-deployment assembly 32 is fully retracted as best seen in FIG. 11, the sidecar carrier 34 blocks the retention tab 132 on the rear ramp 26. When the spike-deployment assembly 32 is fully advanced forward as best seen in FIG. 12, the sidecar carrier 34 releases the retention tab 132 of the rear ramp 26, which blocks the spike-deployment assembly 32 from translating backward, thereby keeping the spikes 38, 42 deployed. The presence of the auto-lock retention tab 132 reduces the need for an additional locking step to retain the spikes 38, 42.

In an exemplary embodiment, the full carrier assembly 32 is self-contained in the spacer body. In this manner, separate spikes or other anti-repulsion elements are not needed to secure the device 10. Although the dovetail 130 and retention tab 132 are exemplified herein, it will be appreciated that locking the spikes 38 in the deployed configuration may be achieved in a number of ways. For example, an alternative way of achieving the same function may include positioning the sidecar carrier 34 or the carrier endplate assembly 32 on the inserter. The inserter is then configured to push the auto-lock mechanism forward and retain the spikes 38, 42 directly.

With further emphasis on FIGS. 11-14, a method of installing the expandable fusion device 10 is shown according to one embodiment. Prior to insertion of the fusion device 10, the intervertebral space is prepared. An intradiscal osteotomy technique may include osteotomy of the posterior elements and ligamentum flavum, and opening a wide access to underlying dural sac and the disc space. Osteotomes may be used to remove posterior osteophytes and the disc. In one method, a discectomy is performed where the intervertebral disc is removed in its entirety or a portion is removed. The endplates of the adjacent vertebral bodies may be scraped to create an exposed end surface for facilitating bone growth across the intervertebral space. The anterior longitudinal ligament (ALL) may be released via spreader or blunt dissection.

One or more endoscopic tubes may be inserted into the disc space. As best seen in FIG. 11, one or more expandable fusion devices 10 may be introduced into the intervertebral space in a collapsed configuration and seated in an appropriate position in the intervertebral disc space. The expandable implant 10 may be placed via a posterior lumbar interbody fusion (PLIF) trajectory.

After the fusion device 10 has been inserted into the appropriate position in the intervertebral disc space, the retention spikes 38, 42 may be deployed as shown in FIG. 12 by translating the sidecar carrier 34 toward the front end 46 of the implant 10. As the sidecar carrier 34 translates forward, the upper and lower carrier endplates 36, 40 translate forward as guided by the tusks 114. The spikes 38, 42, which are pivotably connected to the carrier endplates 36, 40 translate forward and pivot outwardly into the deployed configuration.

Figure 13:
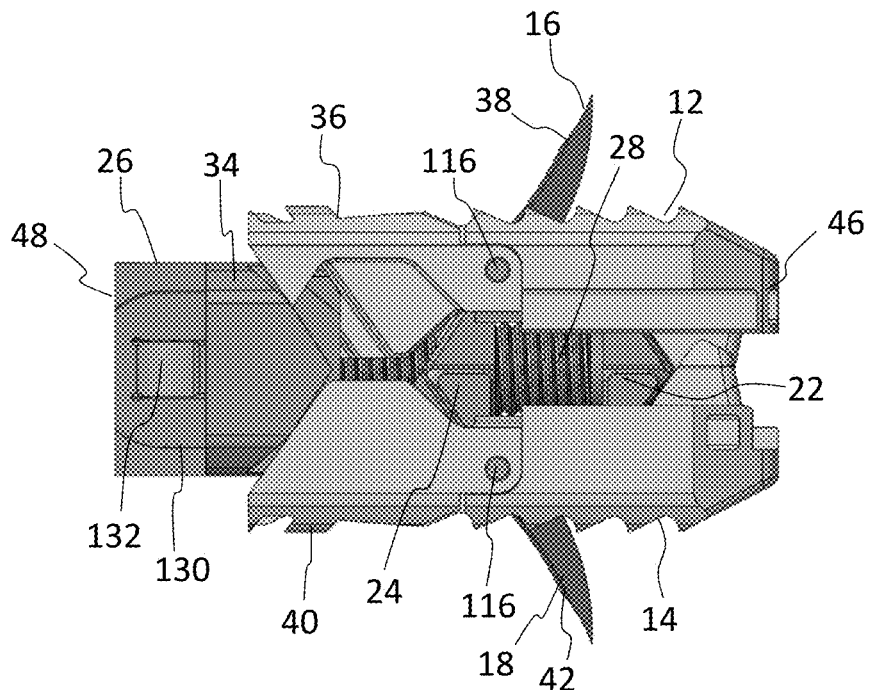
FIG. 13 shows a side view of the implant expanded in a parallel configuration with the retention spikes deployed.
Figure 14:
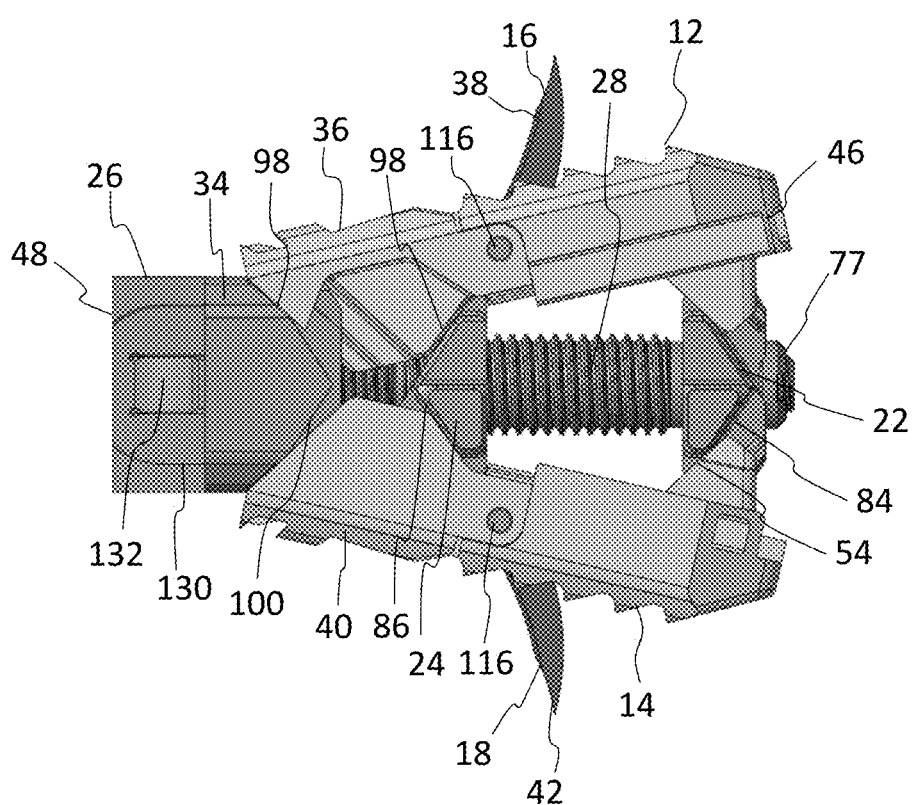
FIG. 14 shows a side view of the implant fully expanded in height with lordotic expansion and the retention spikes deployed.
Figure 15:
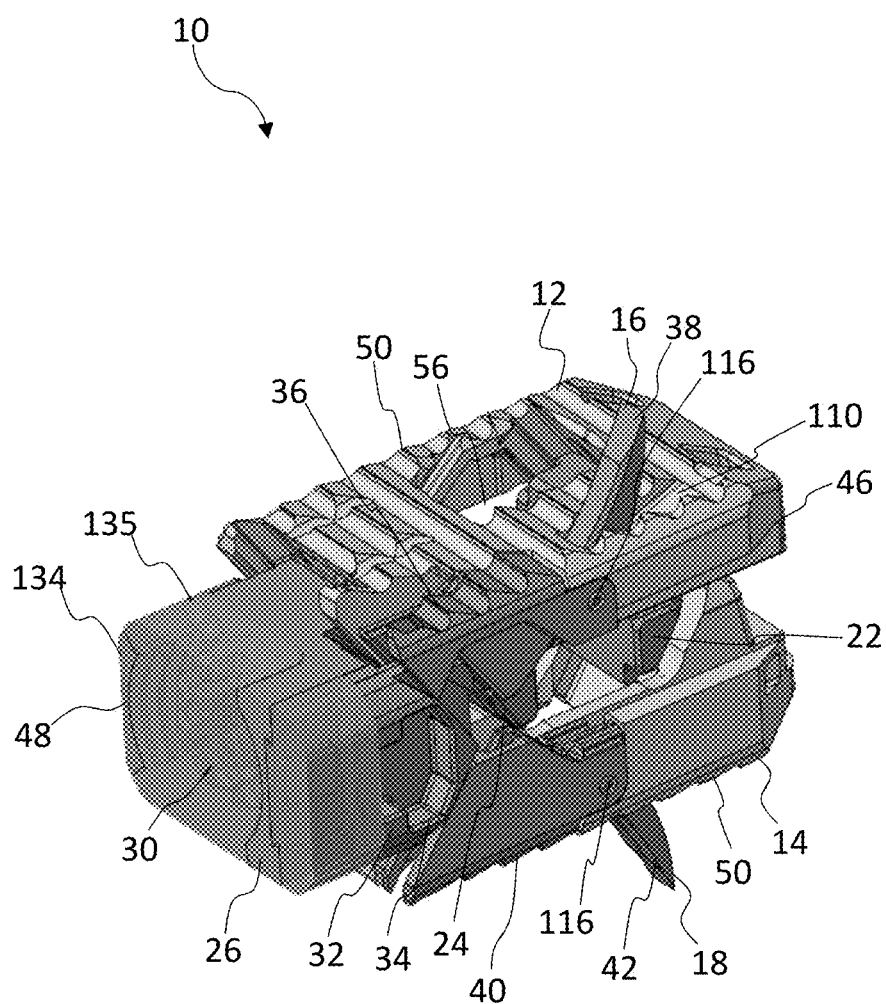
FIG. 15 shows a perspective view of the implant expanded in parallel with the retention spikes deployed and a housing for internal electrical components according to one embodiment.

The fusion device 10 may be expanded in height into the expanded position before or after deploying the spikes 38, 42. As shown in FIG. 13, the endplates 12, 14, 36, 40 may be expanded in parallel. As shown in FIG. 14, the endplates 12, 14, 36, 40 may be expanded in a lordotic configuration. The expandable spacer 10 provides for independent adjustable height and lordosis, which allows the user to fine-tune the final profile to meet the unique anatomy of the patient.

Rods may be reduced into screws placed prior to the osteotomy, and the screws compressed. As the screws are brought closer together, the vertebral bodies may rock about the fulcrum created by the interbody spacers, and segmental lordosis is increased, yielding the desired correction.

Turning now to FIGS. 15-18, expandable fusion device 10 is shown according to one embodiment with one or more electrical components 136 for manipulating the implant 10 and/or communicating with a robotic system 138. Robotic and/or navigated assistance may be used to pre-plan and increase accuracy/efficiency in the placement of the interbody implant and fixation. The orientation and position of the implant 10 in its final implanted position may be optimized with pre-op and intra-op scans utilizing robotic and/or navigational systems. Robotic and/or navigation guidance may be used to correctly orient the implant and align the implant for the desired expansion and deployment of the integrated spikes 16, 18.

Robotic technology may use imaging taken prior to placement of an interbody implant for initial registration. The procedure may rely on direct visualization of motion markers to relay real-time position of instruments and devices, which is overlaid on the initial imaging. As a result, once an interbody is placed, the expansion and resulting change in anatomy position may no longer be reflected on the navigation display. Accordingly, there is a need for an implant that can relay its position and orientation to a computer in a way that does not require direct visualization. In addition, or alternatively, with a large number of independently adjustable features and a small working corridor, there is a need for a device that is autonomously adjustable without requiring direct mechanical interaction with the implant 10.

Figure 18:
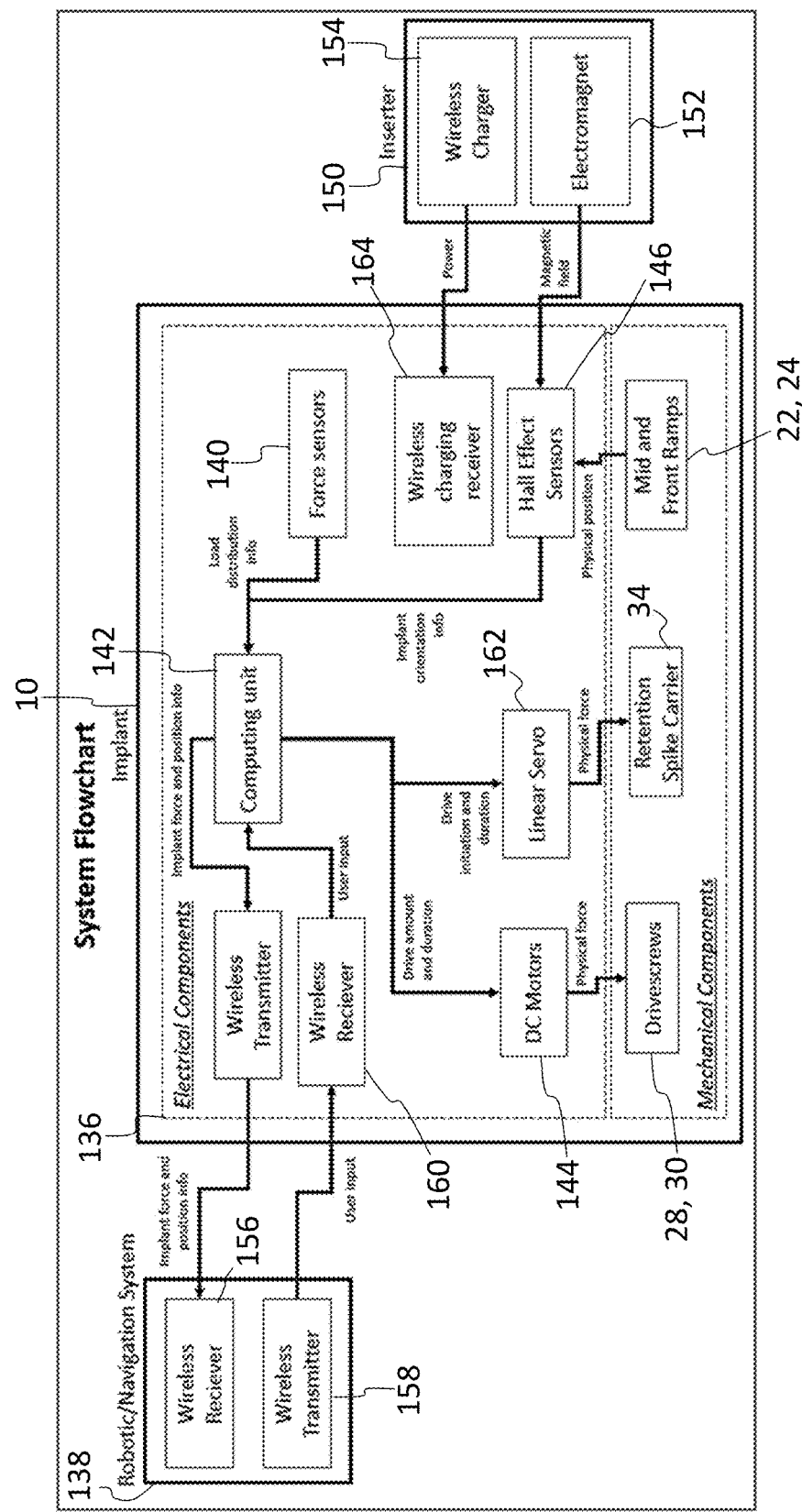
FIG. 18 is a system flowchart depicting the electrical and mechanical components of the implant, a robotic/navigation system interface, and an inserter interface according to one embodiment.

According to one embodiment, the implant 10 is configured to communicate implant position and orientation to the robot 138 before, during, and after the implant 10 expands. FIG. 18 depicts one example of a system flowchart showing implant 10 with embedded electrical components 136, inserter 150 with electromagnet 152 and wireless charger 154 configured to install the implant 10, a robotic/navigation system 138 with a wireless receiver 156 and a wireless transmitter 158 configured to transmit to and receive information from the implant 10, and the mechanical components of the implant 10 including the drive screws 28, 30, the retention spike carrier 34 for deploying spikes 38, 42, and the driving ramps 22, 24 for adjusting the height and lordosis. It will be appreciated that the electrical components 136 in the implant 10 are electrically coupled or connected to one another in a suitable manner to transfer energy, power, and/or information between the components.

The robotic and/or navigation system 138 may include a surgical robot system with an end-effector coupled to a moveable robot arm, a control device (for example, a computer having a processor and a memory coupled to the processor) for controlling the robot arm and end effector, and a display for receiving user inputs and displaying information to the user. The end effector may be configured to hold and/or guide the inserter 150 during the operation. The robotic/navigation system 138 includes wireless receiver 156 to receive information from the implant 10, such as implant force and position information, and wireless transmitter 158 which transmits user input to the implant 10. Further details of robotic and/or navigational systems can be found, for example, in U.S. Pat. Nos. 10,675,094, 9,782,229, and U.S. Patent Publication No. 2017/0239007, which are incorporated herein by reference in their entireties for all purposes.

According to one embodiment, the spacer 10 is capable of relaying its position to the robotic and/or navigation system 138, which overcomes significant obstacles associated with pre-operative imaging when registration is lost after placement of the spacer 10. In addition, the spacer orientation, location, expansion, and/or deployment may be tracked in real-time to better inform the navigated procedure following spacer placement.

The implant 10 may include electrical components 136, such as sensors 140, 146, a memory/storage/computing device 142, actuators 144, 162, a power supply 164, and wireless communication system 160, embedded in various components throughout the spacer 10. The implant 10 may include an outer housing 135 configured to receive, for example, the computing unit 142, motors to actuate the drive screw 28, 30, wireless communications unit 160, linear servo 162 to actuate the sidecar carrier 34, and wireless charger 164 for providing power to the device 10.

The electronic components 136 may be responsible for up to three main operations: (1) measurement of force distribution across the implant 10; (2) subsequent adjustment of implant height and lordosis; and/or (3) the monitoring and communication of implant position and load. The end effector of the robot 138 and/or a user may hold an inserter 150 for positioning the implant 10. The wireless charger 154 in the inserter 150 may be used to wirelessly provide power to the implant 10, and the electromagnet 152 may be used to aid in the positional sensing by the implant 10.

Figure 16:
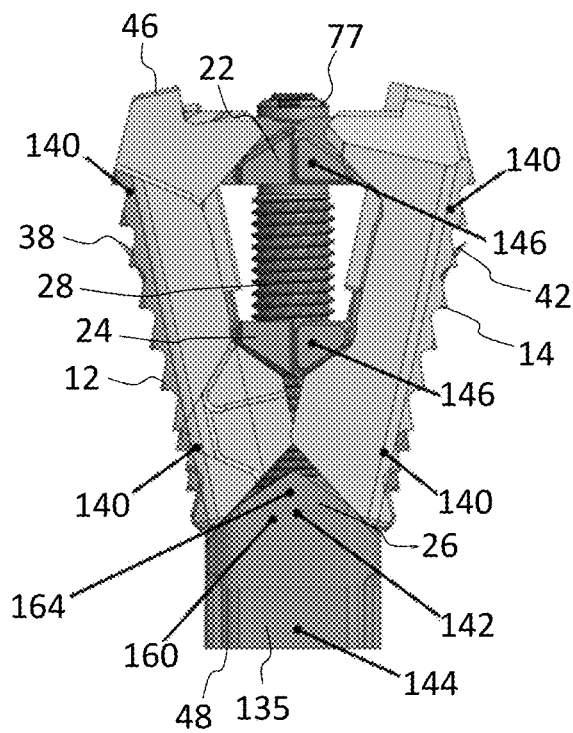
FIG. 16 shows a side view of the implant illustrating electronic component housing locations according to one embodiment.
Figure 17:
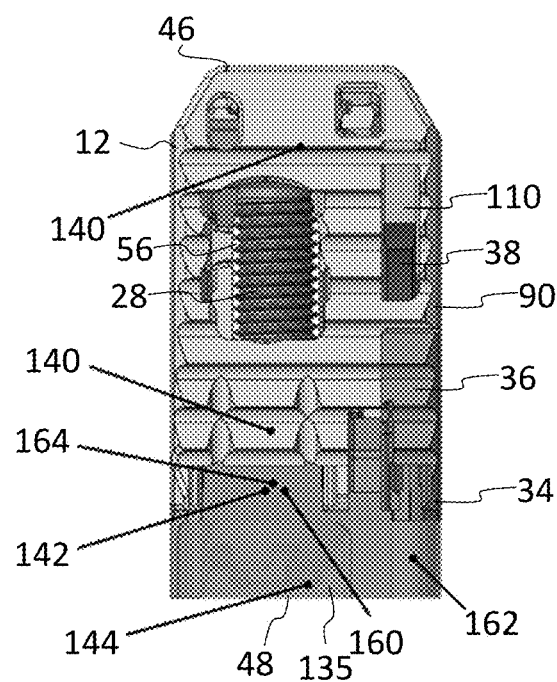
FIG. 17 shows a top view of the implant illustrating electronic component housing locations according to one embodiment.

As best seen in FIGS. 16-17, one or more force sensors 140 may be contained in or on the main endplates 12, 14. For example, the force sensors 140 may be housed in the anterior and posterior portions of both the top and bottom main endplates 12, 14. The force sensors 140 may be responsible for load distribution measurement.

The computing unit 142 may be contained in the implant 10, for example, in the rear ramp 26. The computing unit 142 may include a processor or processing unit with memory, storage, and/or software. The computing unit 142 may be configured to monitor the relative forces over time to judge load distribution. The computing unit 142 feeds this load distribution information through an algorithm to determine appropriate height/lordosis change and rate of change.

Once the determination had been made, the computing unit 142 informs one or more electrical motors 144 to adjust the height of the implant 10. For example, a pair of DC motors 144 may be provided in the housing 135 behind the two drive screws 28, 30. The computing unit 142 may provide information including the drive amount and duration to the motors 144. The motors 144 are configured to automatically drive or rotate the two screws 28, 30 to provide the desired amount and type of expansion to the upper and lower endplates 12, 14.

The implant 10 may include one or more hall effect sensors 146. For example, the hall effect sensors 146 may be housed on or in the front and mid ramps 22, 24, respectively. A separate electromagnet 152 may be provided on the inserter instrument 150, for example. As the electromagnet 152 generates a small magnetic field, the hall effect sensors 146 detect the relative location of the front and mid ramps 22, 24 from the rear ramp 26, which is rigidly constrained to the inserter 150. For any given relative position of the front, mid, and rear ramps 22, 24, 26, there is a single known position and orientation of the main endplates 12, 14. In this way, the location of the ramps 22, 24 as read from the hall effect sensors 146 yields enough information to project real-time implant position status. This information may be projected on the display of the robotic/navigation system 138 after the sensor information is processed by the computing unit 142. The information may be sent wirelessly through the wireless communication unit 160, also identified as wireless transmitter and wireless receiver on the system flowchart. The wireless communication unit 160 may be housed in the body of the rear ramp 26, for example.

When the user confirms final placement of the implant 10, a command is issued by the user and received by the wireless communication unit 160 to initiate deployment. The computing unit 142 provides information to the linear servo motor 162 including drive initiation and duration. The linear servo motor 162 may be housed behind the sidecar carrier 34, which pushes the carrier 34 forward, thereby deploying the retention spikes 38, 42.

Throughout operation, the inserter 150 may include wireless charger 154 on the end, which interfaces with receiving charger 164. The receiving charger 164 may be housed in the rear ramp 26, for example, and provides a power supply for automatic operation of the implant 10. In this manner, the spacer 10 is capable of autonomously driving itself, which reduces the need for multiple drivers to drive anterior and posterior height, as well as anchor deployment. This simplifies operative workflow and increases efficiency of spacer placement. The reduction of multiple instruments may also reduce the required working corridor, tissue disruption, and improving patient recovery time.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An expandable implant comprising:
   upper and lower main endplates configured to engage adjacent vertebrae;
   an actuator assembly configured to cause an expansion in height of the upper and lower main endplates; and
   a sidecar assembly including a sidecar carrier, an upper carrier endplate pivotably coupled to an upper spike, and a lower carrier endplate pivotably coupled to a lower spike, wherein forward translation of the sidecar carrier pushes against the upper and lower carrier endplates, thereby deploying the upper and lower spikes
   wherein the upper carrier endplate includes a first tusk and the lower carrier endplate includes a second tusk, and the first and second tusks extend toward a front of the implant.

2. The expandable implant of claim 1, wherein the first and second tusks are receivable in respective passageways in the upper and lower main endplates to thereby guide translation of the upper and lower carrier endplates.

3. The expandable implant of claim 2, wherein the first and second tusks have a polygonal cross-section that corresponds to the shape and dimensions of the respective passageway.

4. The expandable implant of claim 3, wherein the first and second tusks allow for translation of the upper and lower carrier endplates with respect to the main endplates along a main longitudinal axis of the implant but restricts all other translation and rotation.

5. The expandable implant of claim 1, wherein each spike extends from a proximal end coupled to the respective carrier endplate to a free end, and wherein the free end is pointed and configured to pierce bone.

6. The expandable implant of claim 1, wherein each of the upper and lower main endplates include a side extension portion defining a side channel, wherein the side channels house and guide the upper and lower spikes, respectively.

7. The expandable implant of claim 6, wherein each spike is connected to the respective carrier endplate with a pin, thereby providing a hinged coupling between the carrier endplate and the spike.

8. The expandable implant of claim 7, wherein when the carrier endplates move forward, the spikes bottom out on a floor of the channels, rotating about an axis of the pins connecting the spike to the carrier endplate, and the spikes emerge from top and bottom planes of the main endplates.

9. An expandable implant comprising:
upper and lower main endplates configured to engage adjacent vertebrae;
an actuator assembly including a rotatable actuator having a shaft and a rotatable nut;
a plurality of driving ramps including a front ramp, a mid-ramp, and a rear ramp positioned along the shaft of the actuator, wherein the upper and lower main endplates are engaged with the plurality of driving ramps, and wherein rotation of the actuator and/or the nut causes movement of one or more of the driving ramps, thereby causing an expansion in height of the upper and lower main endplates; and
a sidecar assembly including a sidecar carrier, an upper carrier endplate pivotably coupled to an upper spike, and a lower carrier endplate pivotably coupled to a lower spike, wherein forward translation of the sidecar carrier pushes against the upper and lower carrier endplates, thereby deploying the upper and lower spikes;
wherein the rear ramp includes a retention tab configured to prevent retraction of the spikes by preventing movement of the sidecar carrier.

10. The expandable implant of claim 9, wherein the rear ramp includes a bore for receiving the actuator assembly and a pair of arms positioned on opposite sides of the bore.

11. The expandable implant of claim 10, wherein the rear ramp includes a dovetail slot along an outside face of one arm, and the sidecar carrier includes a corresponding dovetail that mates with the dovetail of the rear ramp, allowing the sidecar carrier to translate with respect to the rear ramp along a main longitudinal axis of the implant while restricting all other translation or rotation.

12. The expandable implant of claim 11, wherein the dovetail slot decreases in height towards a back of the rear ramp.

13. The expandable implant of claim 9, wherein the retention tab is defined by a relief cut that protrudes outward from a side face of the rear ramp, and when the sidecar carrier passes over the retention tab, the retention tab springs outwardly to prevent the sidecar carrier from travelling backwards.

14. The expandable implant of claim 9, wherein each of the upper and lower main endplates include a side extension portion defining a side channel, wherein the side channels house and guide the upper and lower spikes, respectively.

15. The expandable implant of claim 14, wherein when the sidecar carrier translates forward, the carrier endplates move forward, the spikes bottom out on a floor of the channels, rotating and driving the spikes outwardly from top and bottom planes of the main endplates.

16. An expandable implant comprising:
upper and lower main endplates configured to engage adjacent vertebrae;
an actuator assembly including a rotatable actuator and a driving ramp positioned along the actuator configured to cause an expansion in height of the upper and lower main endplates; and
integrated retention spikes deployable from the upper and lower main endplates, wherein the integrated retention spikes deploy when a sidecar carrier is translated forward, pushing against upper and lower carrier endplates that are pivotably coupled to the respective retention spikes
wherein anterior and posterior heights of the implant are independently adjustable for continuous adjustment of height and lordotic profile.

17. The expandable implant of claim 16, wherein the retention spikes maintain a constant penetration depth out of the upper and lower main endplates regardless of height or lordotic expansion.

* * * * *